(12) United States Patent
Hsiue et al.

(10) Patent No.: US 9,091,699 B2
(45) Date of Patent: Jul. 28, 2015

(54) MICROFLUID TESTING SYSTEM WITH A MULTIPLE-CHANNEL DISC AND UTILITY THEREOF

(71) Applicant: Chung Yuan Christian University, Tao-Yuan (TW)

(72) Inventors: Ging-Ho Hsiue, Taipei (TW); Shia-Chung Chen, Taipei (TW); Wen-Tyng Li, Taipei (TW); Yaw-Jen Chang, Taipei (TW); Yung Chang, Taipei (TW); Yi-Hua Fan, Taipei (TW); Ming-Fa Hsieh, Taipei (TW); Wei-Liang Liao, Taipei (TW); Ching-En Chen, Taipei (TW); Ching-Wei Huang, Taipei (TW); Ying-Ming Liang, Taipei (TW)

(73) Assignee: CHUNG YUAN CHRISTIAN UNIVERSITY, Tao-Yuan (TW)

( * ) Notice: Subject to any disclaimer, the term of this patent is extended or adjusted under 35 U.S.C. 154(b) by 129 days.

(21) Appl. No.: 13/863,705

(22) Filed: Apr. 16, 2013

(65) Prior Publication Data

US 2014/0186963 A1 Jul. 3, 2014

(30) Foreign Application Priority Data

Dec. 28, 2012 (TW) .............................. 101150806 A (51) Int. Cl.
*G01N 33/00* (2006.01)
*G01N 33/80* (2006.01)
*B01L 3/00* (2006.01)

(52) U.S. Cl.
CPC .......... *G01N 33/80* (2013.01); *B01L 3/502746* (2013.01); *B01L 2200/0621* (2013.01); *B01L 2300/0803* (2013.01); *B01L 2300/0867* (2013.01); *B01L 2400/0409* (2013.01); *B01L 2400/0688* (2013.01); *B01L 2400/084* (2013.01)

(58) Field of Classification Search
USPC .................................................... 422/506, 73
See application file for complete search history.

(56) References Cited

U.S. PATENT DOCUMENTS

2008/0108120 A1* 5/2008 Cho et al. ................... 435/173.7
2010/0240142 A1* 9/2010 Saiki et al. ................... 436/164

* cited by examiner

*Primary Examiner* — Jill Warden
*Assistant Examiner* — Brittany Fisher
(74) *Attorney, Agent, or Firm* — WPAT, PC; Justin King (57) ABSTRACT

The present invention discloses a system for testing microfluid which is made with a disposable disc. The high sensitivity, high sensing accuracy, and quick response microfluidic disc is demonstrated in the present invention. It is note that easy to test microfluid without traditional detecting method, and then reduce energy and simplify procedure. Furthermore, to additive the microfluidic disc is useful to enhance blood typing, and hence raising the sensitivity by the video recognition of blood agglutination.

10 Claims, 6 Drawing Sheets

MICROFLUID TESTING SYSTEM WITH A MULTIPLE-CHANNEL DISC AND UTILITY THEREOF

BACKGROUND OF THE INVENTION

1. Field of the Invention

This invention generally relates to the field of fluid testing system, and more particularly, to a multichannel microfluidic disc testing system and utility thereof.

2. Description of the Prior Art

Nowadays, the examination of specific biofluid is often needed as a basis for diagnosis in biomedical field. Currently, one of the known blood identification methods is microplate method, which has been used extensively in various medical examinations.

This method requires manual operation on a 96-well plate; therefore, it consumes a lot of time, manpower, specimens and reagents. In all kinds of medical products and researches, such as blood test, body fluid test and medical reagent test, etc, biofluid is often used to run the test, for example, blood typing test, disease diagnostic test and the screening of medicament in development. Generally speaking, these specimens and reagents tend to be few, expensive and are not easy to obtain. If these specimens and reagents are over-consumed and are not run correctly, it will cause failure in examination and prevent the next correct medical treatment from happening; it will also cause failure in the experiment and the development of medical treatment or medicine will be delayed. In order to protect human bodies from being drawn a large quantity of blood or specimens because of the need of test, accurate test and analysis with a small quantity of specimens is extremely important.

The researches of microfluidic method have been used extensively on various kinds of medical tests. Jeong-gun et al. presented their patent "CENTRIFUG MAGNETIC POSITION CONTROL DEVICE, DISK-SHAPED MICRO FLUIDIC SYSTEM INCLUDING THE SAME, AND METHOD OF OPERATING THE COMPACT DISK-SHAPED MICRO FLUIDIC SYSTEM" and disclosed a disposable multichannel microfluidic plate that can be used to run fluid identification. Per Andersson et al. presented their patent "SEPARATION STRUCTURE" and disclosed a disposable multichannel microfluidic plate that can be used to run fluid identification. The following are some drawbacks of the common technological principles of multichannel microfluidic plate: it only runs single test; it requires a large quantity of fluid sample and reagents; it is hard to analyze; it is difficult to test and the test strips are complicated to produce and prepare, etc. These drawbacks have lead to high cost and long testing hours; especially the single test can only focus on one testing target, which is really minute and complicated. Therefore, it is still hard to use the current methods extensively in the fields of medical research, biochemical analyses and clinic diagnoses.

Based on this, the important target of current industries is to develop a biofluid testing system that can simplify these multiple steps and examine many items simultaneously to lower the usage of a large quantity of fluid samples and reagents, to analyze easily, to examine conveniently and to produce and prepare the test strips simply, thus, the cost and the working hours can be lowered.

SUMMARY OF THE INVENTION

In accordance with the present invention, a multichannel microfluid disc testing system and utility thereof substantially obviates one or more of the problems resulted from the limitations and disadvantages of the prior art mentioned in the background.

One of the present invention's objectives is to provide a multichannel microfluidic disc testing system to examine the component and the density of biofluid waiting to be examined. This multichannel microfluidic disc testing system combines a disposable disc module with a "multichannel microfluidic disc testing image recognition and measurement system", which includes a dosing module, a spinning module, a testing module, an analysis/control module and an energy module. This multichannel microfluidic disc testing system specially designed the disposable testing disc. After adding specimens and different testing reagents onto the disc, the centrifugal mixing is proceeded to form reactants. The factors waiting to be detected in the reactants will have different coagulations, and the differences among the coagulations can be utilized to mark the specimens whose factors are waiting to be detected.

The multichannel microfluidic disc testing system provided by the present invention combines "the disposable disc module" with "the multichannel microfluidic disc testing image recognition and measurement system". The disc module of the testing system in the present invention has a testing mechanism including at least one vent aperture, at least one vent chamber, at least one feeding aperture, at least one feeding chamber, at least one reaction chamber, at least one reaction testing zone, at least one waste chamber, at least one microfluidic channel, and at least one capillary valve. The design of the multichannel microfluidic disc testing system makes use of the resistant characteristic produced by the fluid's surface tension on the disposable disc, in the accommodating space where the specimens and reagents are being added, the resistance of different fluids' surface tensions is broken according to the speed of the centrifugal force. Then the specimens and the reagents flow into the reaction space to mix and form the reactants. With the changes of reagents, different formations of the coagulations are produced to confirm the existence and the density of the factors waiting to be examined in the specimens.

The disc module production of the present invention adopts traditional low-cost technology, using at least one transparent substrate which is produced and prepared by carving or injection molding. Through the calibration and calculation of the built-in software in the multichannel microfluidic disc testing system, the instrument will directly show the type and the density of the factors waiting to be examined. In addition, the multichannel microfluidic disc testing system uses the disposable disc module, so it won't be easily damaged by the pollution of the specimens and reagents. The reliability will be greatly enhanced and the longevity of this system will also be prolonged substantially. The multichannel microfluidic disc testing system can be installed in medical facilities and laboratories which have the need to test few or important specimens. The multichannel microfluidic disc testing system is composed of the disposable disc module and the multichannel microfluidic disc image recognition system. Due to its simple production of the disc module, convenient testing process, low cost, lower environment limit, the present invention and its skill advantages are more advantageous than other common microplate methods. At the same time, it requires extremely few specimens and reagents, and the testing is fast. Moreover, compared with the traditional manual matching and analysis, the operators of the present invention can use it by themselves and directly read the statistics to make judgments without being equipped with professional knowledge of medicine or chemistry.

Another objective of the present invention is to provide a kind of disposable disc, which is composed of at least one transparent substrate and at least one testing mechanism. The testing mechanism includes at least one feeding aperture, at least one vent chamber, at least one feeding chamber, at least one reaction chamber, at least one reaction testing zone, at least one waste chamber, at least one microfluidic channel and at least one capillary valve. They are manufactured and prepared by carving or injection molding, and this process can be operated in the common environment. The structure of the testing mechanism can be designed according to the coagulation formation process of the factors waiting to be examined. The disc module of the present invention is disposable so the production is inexpensive and is easy to operate.

The current microplate methods and traditional manual operations cost a bit higher and consume more specimens and reagents. To overcome the drawbacks of the past biofluidic testings, the present invention has the following advantages: low cost, convenient operation, smaller quantity of specimens and reagents, and shorter reaction time. It is to replace the traditional multichannel microfluidic disc testing system. The present invention can lower the quantity of specimens, reagents and shorten reaction time, so the tests of the existence and density of the factors waiting to be examined in the specimens can be run fast with a low quantity of specimens and reagents, which is a very practical and convenient testing device for medical facilities and laboratories.

According to the abovementioned objectives of the present invention, it provides a multichannel microfluidic mechanism which includes at least one feeding chamber that is an accommodating space storing microfluids transported from the exterior; and at least one reaction chamber which receives the microfluids discharged from the feeding chamber under centrifugal state to carry out the reaction.

The abovementioned feeding chamber connects with the exterior atmosphere under centrifugal state to form a vent chamber to allow the microfluids to flow under centrifugal state. The abovementioned reaction chamber includes at least one reaction testing zone which stores the microfluidic reactants to facilitate the collection and analysis of the images of the reactant coagulations. The multichannel microfluidic mechanism further includes at least one microfluidic channel to connect the feeding chamber and the reaction chamber and transport the microfluids under centrifugal state.

The abovementioned microfluidic channel has a specific bending angle which can control the discharging rate of the microfluids through the centrifugal rotational speed, and prevent reverse flow of the microfluids. Wherein, the smaller the bending angle is, the bigger the resistance of the reverse flow is. The abovementioned reaction chamber further includes at least one waste chamber to receive the waste fluid from the reaction chamber. The abovementioned microfluidic channel connects the reaction chamber with the waste chamber, and forms a level inclination at the connection. Wherein, the microfluidic channel exit near the waste chamber should be higher than the microfluidic channel entrance near the reaction chamber to prevent reverse flow of the microfluids. There is a specific joint angle at the connection between the abovementioned microfluidic channel and the feeding chamber, which controls discharging rate of the microfluids through the centrifugal rotational speed, and prevents reverse flow of the microfluids. There is a capillary valve at the connection between the abovementioned microfluidic channel and the feeding chamber, which controls the discharging rate of the microfluids through the centrifugal rotational speed, and prevents reverse flow of the microfluids. The abovementioned capillary valve forms an interlocked combination of at least one convex channel and at least one cavernous channel on the microfluidic channel to form a serrated appearance. The diameter of the abovementioned convex channel is bigger than that of the cavernous channel, and the diameter of the convex channel is also bigger than that of the microfluidic channel.

Based on the abovementioned objectives of the present invention, it provides a multichannel microfluidic disc which has at least one testing mechanism that includes at least one feeding chamber, an accommodating space for microfluids imported from the exterior; at least one reaction chamber, a reaction space receiving the microfluids discharged from the feeding chamber under centrifugal state to allow the microfluids to react; at least one waste chamber, which receives the microfluids from the reaction chamber under centrifugal state; and a plurality of microfluidic channels which connect the feeding chamber with the reaction chamber, and connects the reaction chamber and the waste chamber respectively. The abovementioned testing mechanism further includes at least one vent chamber, which is a space connecting the atmosphere to allow the microfluids to flow in the testing mechanism under centrifugal state. The abovementioned reaction chamber includes at least one reaction testing zone, which is used to store the reactant of the microfluid and collect and analyze the images of the reactant coagulations. The abovementioned microfluidic channel has a specific bending angle which controls the discharging rate of each microfluids through the centrifugal rotational speed and prevents reverse flow of the microfluids. The abovementioned microfluidic channel connects the reaction chamber and the feeding chamber, and forms a level inclination angle. Wherein, the microfluidic channel exit near the waste chamber should be higher than the microfluidic channel entrance near the reaction chamber to prevent reverse flow. There is a specific joint angle at the connection between the abovementioned microfluidic channel and the feeding chamber, which controls discharging rate of the microfluids through the centrifugal rotational speed, and prevents reverse flow of the microfluids. There is a capillary valve at the connection between the abovementioned microfluidic channel and the feeding chamber, which controls the discharging rate of the microfluids through the centrifugal rotational speed, and prevents reverse flow of the microfluid. The abovementioned capillary valve forms an interlocked connection of at least one convex channel and at least one cavernous channel on the microfluidic channel to form the serrated appearance. The diameter of the convex channel is bigger than that of the cavernous channel, and the diameter of the convex channel is also bigger than that of the microfluidic channel. The diameter of the abovementioned cavernous channel is smaller than that of the microfluidic channel. The diameter of the abovementioned convex channel is 60-800 micrometer, and that of the cavernous channel is 50-600 micrometer. The ratio of the diameter of the abovementioned convex channel and that of the cavernous channel is 2:1-5:1. The better diameter of the abovementioned convex channel is 300 micrometer. The better diameter of the abovementioned cavernous channel is 100 micrometer. The spatial depth of the abovementioned feeding chamber, reaction chamber, waste chamber, microfluidic channel and the capillary valve is 50-1000 micrometer.

Based on the abovementioned objectives of the present invention, it provides a multichannel microfluidic disc testing system which includes a disc module, used to receive a plurality of microfluidic reagents, by way of centrifugal effect, a plurality of microfluidic reagents are mixed in the disc module to produce chemical effect and form reactants; a dosing module, located in a specific place on the rotating direction of the disc module, and the dosing module provides a plurality of microfluidic reagents and centrifugal effect to the disc module; and an imaging module, located in a assigned place on the upper part of the disc module, collects the images of the reactant coagulations on the disc module and produces an image signal. The abovementioned dosing module further includes at least one dosing device, used to control the placing, loading, transporting and infusing of a plurality of microfluids to the disc module; at least one spinning device, used to provide the disc module with the spinning kinetic energy to carry out the centrifugal motion, makes a plurality of microfluidic reagents mix and react on the disc module by way of centrifugation. The abovementioned disc module includes at least one testing unit, which further includes a plurality of feeding chambers that are used to respectively receive and store a plurality of microfluidic reagents provided by the dosing module; at least one reaction chamber, which is used to respectively receive a plurality of microfluidic reagents discharged by a plurality of feeding chambers to carry out the reaction and form the reactants, wherein, the imaging module is located in an assigned place on the upper part of the reaction chamber to collect the images of the reactant's coagulations; and a plurality of microfluidic channels, which are used respectively to connect the feeding chambers and the reaction chamber. The appearance of the abovementioned testing unit is dendriform, and a plurality of microfluidic channels are the branches of the dendriform appearance, and a plurality of feeding chambers are located at the end of the branches, and the reaction chambers are located at the root of the dendriform appearance. A first microfluidic channel of the abovementioned microfluidic channels is used as one main trunk and is connected with the reaction chamber. A plurality of the second microfluidic channels of the abovementioned microfluidic channels are treated as the branches and are connected to the first microfluidic channel and the feeding chamber. The second microfluidic channel has a bending angle, which controls the discharging speed of the microfluidic reagents and prevents the reverse flow through the centrifugal speed. The joint angle of the second microfluidic channel and the feeding chamber is a tangential angle, and it lowers the surface resistance by way of tangent line to circle and leads the microfluid out of the feeding chamber centrifugally. The accommodating space of the abovementioned reaction chamber includes at least one reaction testing zone to provide the reaction space for a plurality of microfluidic reagents and stores the reactants to allow the imaging module to collect the images of the reactants' coagulations in the reaction testing zone. The testing unit further includes a plurality of vent chambers which connect to the atmosphere in centrifugal state to allow the microfluidic reagents to flow in centrifugal state. The testing unit further includes at least one waste chamber to receive the microfluid from the reaction chamber in centrifugal state. The reaction chamber connects to the waste chamber by way of the microfluidic channel, which forms a level inclination at the jointing area. The microfluidic channel exit near the waste chamber should be higher than the microfluidic channel entrance near the reaction chamber to prevent reverse flow of the microfluid. There is a capillary valve at the connection between the microfluidic channel and the feeding chamber. It controls the discharging speed of the microfluids through the centrifugal speed and produces anti-kickback effect to the overflowing microfluid. Wherein, the capillary valve forms at least one convex channel and at least one cavernous channel on the microfluidic channel to form a serrated appearance because of their interlocked arrangement. The diameter of the convex channel is bigger than that of the cavernous channel, and the diameter of the convex channel is also bigger than that of the microfluidic channel. Wherein, the diameter of the cavernous channel is smaller than or equal to that of the microfluidic channel. The microfluidic reagents further includes RBC (red blood cell), antibody/plasma, LIM (low ionic medium), polybrene/PEI (polyethyleneimine), resuspending solution, etc. The multichannel microfluidic disc testing system further includes an analysis and control module, which communicate with the dosing module and the imaging module respectively in order to control the actions of the dosing module and the imaging module. Moreover, the analysis and control module receives the image signal from the imaging module and shows the results based on the analysis and matching.

According to the abovementioned objectives of the present invention, it provides a multichannel microfluidic disc testing method, which includes performing a dosing procedure that conducts the microfluids of the specimens and a plurality of reagents to a plurality of feeding chambers on a disc; by controlling the speed of a spinning device to create different centrifugal powers, a centrifugal procedure being performing on the disc, and through this, it controlling the microfluid's discharging speeds in different feeding chambers, wherein the microfluids respectively go through multiple microfluidic channels in centrifugal state to a reaction chamber to proceed the mixing, thus, a reactant is formed in a testing zone in the reaction chamber; and performing a testing procedure by an image collecting device to observe and measure the reactant's coagulation state. The centrifugal procedure further includes a first centrifugal step to conduct a first, a second, and a third microfluid inside the feeding chambers to the reaction chamber, wherein the spinning device reciprocates the disc to proceed a first mixing and blending procedure in the reaction chamber and the first, the second and the third microfluid are mixed and blended to form a first reactant; the second centrifugal step to conduct the fourth microfluid from one of the feeding chambers to the reaction chamber, wherein, by reciprocating the disc, the second mixing and blending procedure is proceeded in the reaction chamber to mix and blend the fourth microfluid with the first reactant, forming the second reactant, and increasing the coagulation reaction; the third centrifugal step to separate the coagulation in the second reactant, leaving most of the specimens and other reagents in the testing zone to mix and form the third reactant; the fourth centrifugal step to conduct the fifth microfluid from one of the feeding chambers to the reaction chamber, and mixed with the third reactant to form the fourth reactant; and the third mixing and blending procedure to coagulate the fourth reactant. The first microfluid is RBC, the second microfluid is antibody/plasma, the third microfluid is LIM, the fourth microfluid is polybrene/PEI, and the fifth microfluid is resuspending solution. The centrifugal speed of the first centrifugal step is 600-800 rpm and the operating time is 1-10 sec; the centrifugal speed of the second centrifugal step is 600-1000 rpm and the operating time is 1-10 sec; the centrifugal speed of the third centrifugal step is 600-1500 rpm and the operating time is 1-10 sec; and the centrifugal speed of the fourth centrifugal step is 600-2000 rpm and the operating time is 1-10 sec. The revolving angle range of the first, the second and the third mixing and blending procedure is from 10 to 360 degrees, and the revolving time is 1-10 times. The testing procedure produces an image by the image collecting device based on the coagulation state of the reactants, and a matching and analyzing procedure is performed. The matching and analyzing procedure is done through a device by analyzing the image signal with the data in a default database, and confirms the coagulation state of the fourth reactant through this.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

Some embodiments of the present invention will now be described in greater detail. Nevertheless, it should be noted that the present invention can be practiced in a wide range of other embodiments besides those explicitly described, and the scope of the present invention is expressly not limited except as specified in the accompanying claims.

Moreover, some irrelevant details are not drawn in order to make the illustrations concise and to provide a clear description for easily understanding the present invention.

Figure 1:
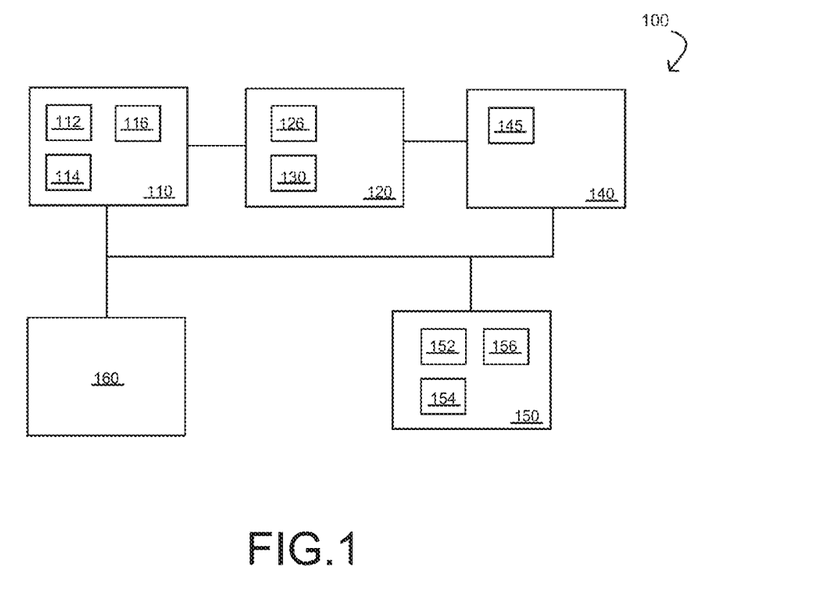
FIG. 1 shows a block diagram of a multichannel microfluidic disc testing system for a first preferred embodiment in accordance with the present invention.

Referring to FIG. 1, according to a first embodiment of the present invention, the present invention provides a multichannel microfluidic disc testing system 100, which includes a dosing module 110, a disc module 120, an image module 140, an analysis and control module 150 and an energy module 160. The abovementioned dosing module 110 further includes at least one transporting device 112, at least one dosing device 114, at least one revolving device 116. Wherein, the dosing module 110 is located in a specific place on the revolving direction of the disc module 120. The transporting device 112 moves the dosing device 114 to provide the reagents to the disc module 120. The revolving device 116 provides kinetic energy to the disc module 120 to proceed the centrifugal motion to enable the reagents to react in the disc module 120. The abovementioned disc module 120 further includes at least one fixed mechanism 126 and one testing mechanism 130. Wherein, the disc module 120 is fixed on the revolving 116 by way of the fixed mechanism 126 to provide a specific space for the reagents provided by the dosing device 114, and at least generates one reactant here so that the image module 140 can collect at least one reactant's image. In addition, the abovementioned image device 140 is located in any appointed place on the disc module 120 to collect the images of the reactant's coagulation on the disc module 120. Moreover, the disc module 120 is disposable in order to avoid being polluted by the specimens and the reagents, so that the reliability of the testing can be greatly enhanced, and that it can prevent the direct contact of the dosing module 110 and the image module 140 to extensively prolong the life of the whole apparatus. The abovementioned analysis and control module 150 respectively communicate with the dosing module 110 and the image module 140 so that the analysis and control module 150 can control the movement, the dosing and the revolving of the dosing module 110. In addition, the analysis and control module 150 can receive the signals produced by the image module 140 so it can analyze and match if the factors being tested exist in the specimens and show the results. The abovementioned energy module 160 respectively couples with each module to provide necessary energy to related operation.

Figure 2A:
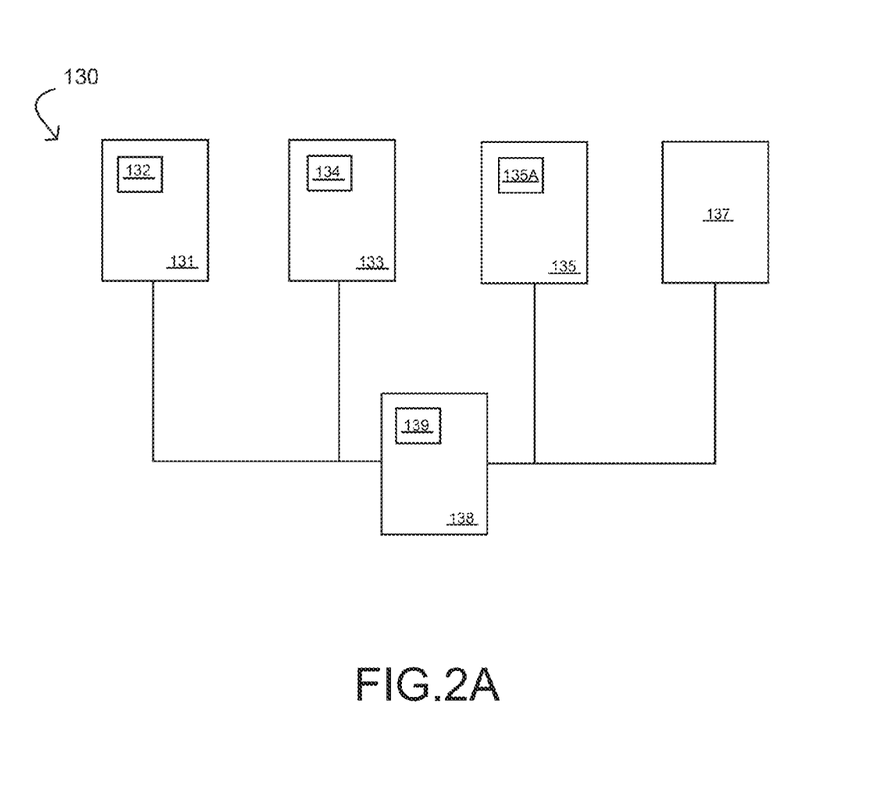
FIG. 2A illustrates a block diagram of a testing mechanism of the multichannel microfluidic disc testing system for the first preferred embodiment in accordance with the present invention.

Referring to FIG. 2A, according to the first embodiment of the present invention, the testing mechanism 130 of the abovementioned disc module 120 includes at least one feeding chamber 131, at least one feeding aperture 132, at least one vent chamber 133, at least one vent aperture 134, at least one reaction chamber 135, at least one reaction testing zone 135A, at least one waste chamber 137, at least one microfluidic channel 138 and at least one capillary valve 139. Wherein, the testing mechanism 130 of the disc module 120 further includes at least one transparent substrate, formed by carving, photo process manufacturing, hot-press method or injection molding, and the testing mechanism 130 is a replaceable one. The abovementioned vent chamber 133 connects with the atmosphere so that the reagents are able to flow in the testing mechanism 130 under centrifugal state. Wherein, the vent aperture 134 is under the vent chamber 133 so it connects with the exterior atmosphere. Moreover, the depth of the abovementioned feeding chamber 133, reaction chamber 135, waste chamber 137, microfluidic channel 138 and the capillary valve 139 is 50-1000 micrometer. The abovementioned feeding chamber 133 is the accommodating space for the solutions added by the dosing device 114. Wherein, the feeding 133 further includes at least one feeding aperture 132 to inject the solutions. The abovementioned reaction chamber 135 receives the reagents from the feeding chamber 133 under centrifugal state to provide a reaction space for the specimens and reagents. Wherein, the reaction chamber 135 includes at least one reaction testing zone 135A, which is in the accommodating space (or called reaction space) of the reaction chamber 135 to keep the reactants of the specimens and other reagents, so that the image module 140 can collect the images of the reactant's coagulation states in the reaction testing zone 135A. The abovementioned waste chamber 137 and the reaction chamber 135 connect with each other to receive the waste fluid from the reaction chamber 135. The abovementioned microfluidic channel 138 respectively connects feeding chamber 131 with reaction chamber 135, connects reaction chamber 135 with the waste chamber 137, connects vent chamber 133 with waste chamber 137, and directly connects with vent chamber 133. Wherein, the connecting entrance of the microfluidic channel 138, the feeding chamber 131 and the waste chamber 137 has a specific joint angle, which can be designed according to the characteristic of the reagents, and control the discharging speed of the specimens and the reagents by centrifugal rotational speed, and prevent reverse flow of the microfluids. The abovementioned capillary valve 139 is located at the entrance of the microfluidic channel 138 that connects feeding chamber 131. The capillary valve 139 can increase the resistance of the fluid coming from the feeding chamber 131 and the reaction chamber 135 under centrifugal state.

Figure 2B:
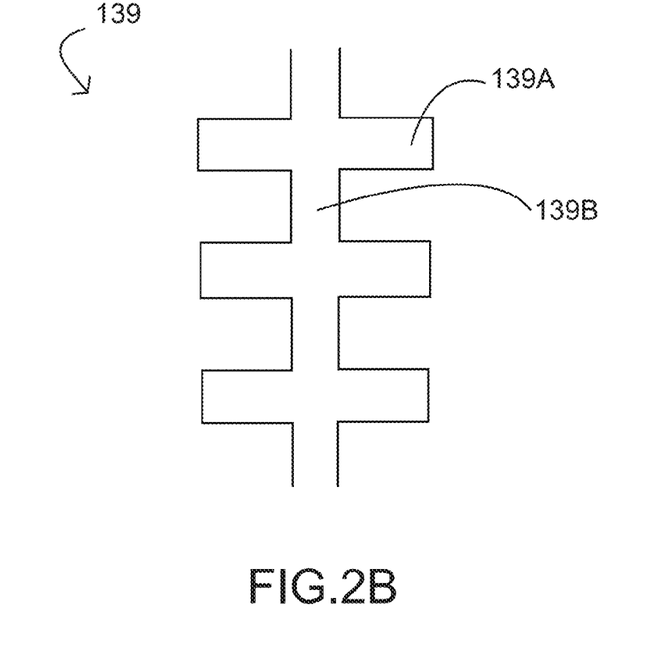
FIG. 2B illustrates the capillary valve of the testing mechanism for the first preferred embodiment in accordance with the present invention.

Referring to FIG. 2B, according to the first embodiment of the present invention, the abovementioned capillary valve 139 forms the connection of at least one convex channel 139A and at least one cavernous channel 139B on the microfluidic channel 138. The capillary valve 139 appears as a serrated structure, and the diameter of convex channel 139A is bigger than that of cavernous channel 139B. The diameter of convex channel 139A is also bigger than the main diameter of microfluidic channel 138. Wherein, the diameter of convex channel 139A is around 60-800 micrometer, and the diameter of cavernous 139B is 50-600 micrometer. The reactants' coagulation states in the abovementioned reaction testing zone 135A change with different reagents in the mixing and blending procedure. The abovementioned imaging module 140 collects the reactants' coagulation states and produces an image signal for the analysis and control module 150 to compare with the coagulation formed in the reaction testing zone 135A when the disc module 120 is in the testing process. Wherein, the density of the reactants will influence the results of coagulation. The lower the density of the reactants are, the fewer the coagulations are. If the reactant's density increases gradually, the coagulation forms will be more. The abovementioned analysis and control module 150 controls the operation of dosing module 110, disc module 120 and the image module 140. The analysis and control module 150 can control the dosing module 110's injection amount, rate, location, and the revolving speed of the disc module 120. Moreover, the analysis and control module 150 includes one analysis unit 152, one control unit 154, and one display unit 156. The analysis and control module 150 receives the electronic signal transmitted by the imaging module 140, calculating and analyzing through the analysis unit 152, and at the same time producing controlling signal through the control unit 154 to control the display unit 156 in order to show the result. Wherein, the analysis unit 152 has a default database, which can provide the matching images of the specific reactants' coagulation forms.

Figure 3:
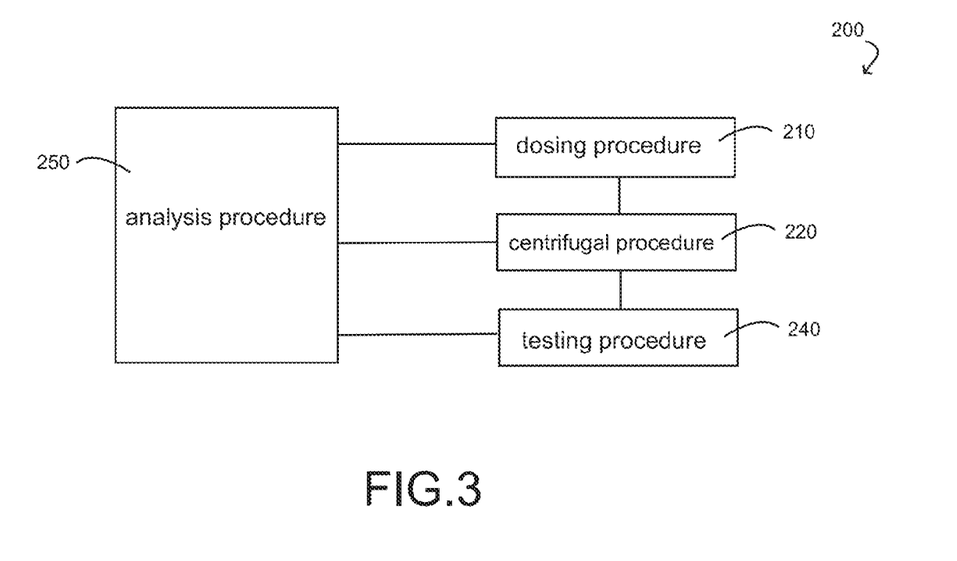
FIG. 3 shows the testing flow chart of the multichannel microfluidic disc testing system for the first preferred embodiment in accordance with the present invention.

Referring to FIG. 3, according to the first embodiment of the present invention, the present invention provides a multichannel microfluidic disc testing method 200. First of all, the disc module 120 is placed on a default position of the dosing module 110, and the follow-up procedure is controlled by the analysis and control module 150's control unit 154. Next, a dosing procedure 210 is carried out by way of dosing module 110 to transmit the microfluids of specimens and reagents to the feeding chamber 131 of the disc module 120. Then, the revolving device 116 of the dosing module 110 revolves the disc module 120 to carry out a centrifugal procedure 220, and the control unit 154 controls the speed of the revolving device 116 to create different centrifugal forces. The control unit 154, by way of centrifugal forces, further breaks through the resistance created by the surface tension of the specimen's and reagent's microfluids injected by the feeding chamber 133, and then guides the microfluids to the microfluidic channel 138, respectively flowing into the reaction chamber 135 to mix and form the reactant and its coagulation. Then by means of the imaging module 140, the testing procedure 240 is proceeded to observe and measure the reactant's coagulation in the reaction testing zone 135A, and a corresponding image signal is produced for the analysis and control module 150. The analysis unit 152 of the analysis and control module 150 will carry out an analysis procedure 250 based on the corresponding image signal to compare and contrast with the reactant's coagulation in analysis module 152's default database, or the numerical value represented by the corresponding reactant's coagulation state, so as to make sure that the specimen contains factors to be examined and produces the information, and at the same time transmits the information to the control unit 154 of the analysis and control module 150, and carries out a control procedure 250 to create a controlling signal, which will be transmitted respectively to the display unit 156 to show that the coagulation of the specimens containing factors to be examined.

Figure 4A:
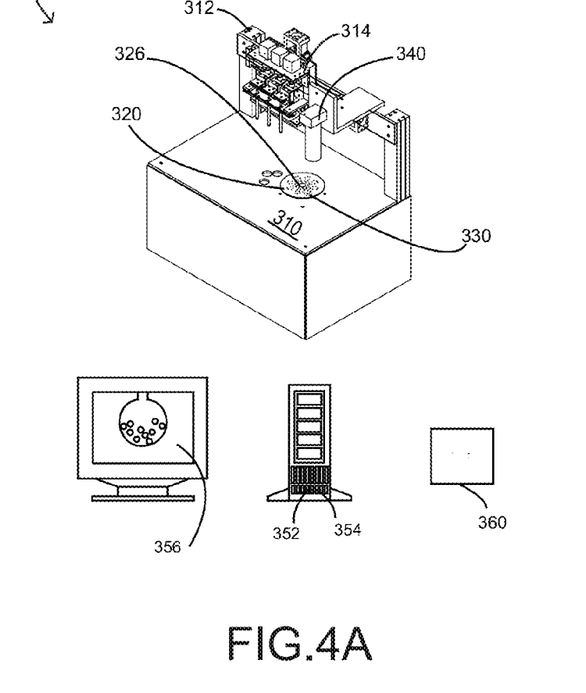
FIG. 4A and FIG. 4B shows a multichannel microfluidic disc testing device for a second preferred embodiment in accordance with the present invention.
Figure 4B:
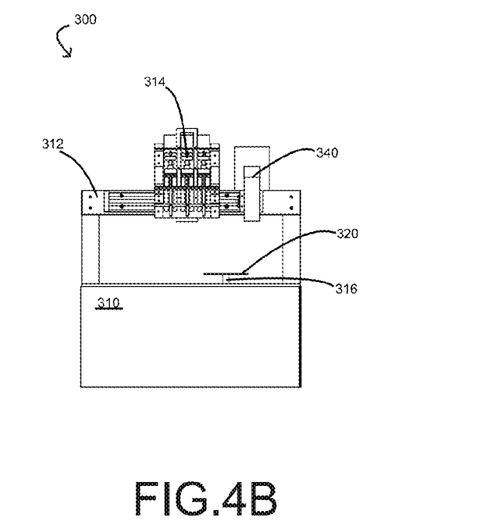

Referring to FIGS. 4A and 4B, according to a second embodiment of the present invention, the present invention provides a multichannel microfluidic disc testing device 300, which includes one supporting mechanism 310, multiple supporting devices 311, at least one moving component 312, at least one dosing component 314, at least one revolving component 316, one disc 320, one image sensing component 345, one analysis component 352, one control component 354, one display component 356 and one power source component 360. The multiple supporting devices 311 are used to support, clip or hold each component, and can directly form in a specific area on the supporting mechanism 310 or can be made separately. The abovementioned moving component 312 is used to transport or move the dosing component 314 so that it can add reagents to the disc 320. The dosing component 314 is used to control storing, loading, transporting and injecting various kinds of microfluid medicaments/reagents to the disc 320 so that they can mix and react on the disc 320. The abovementioned power source component 360 is used to provide power to the whole components of the multichannel microfluidic disc testing device 300.

Figure 5:
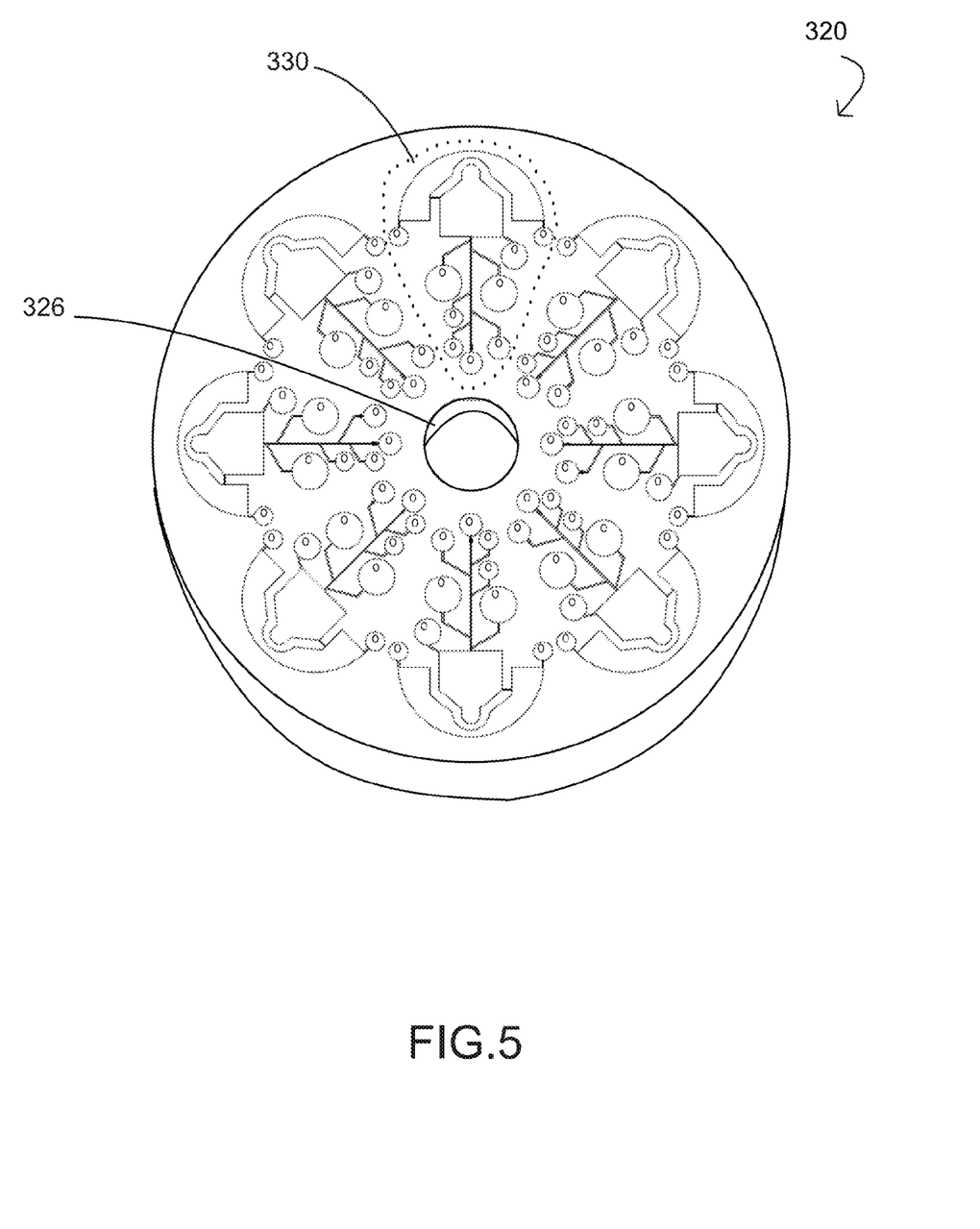
FIG. 5 shows the disc for the second preferred embodiment in accordance with the present invention.
Figure 6A:
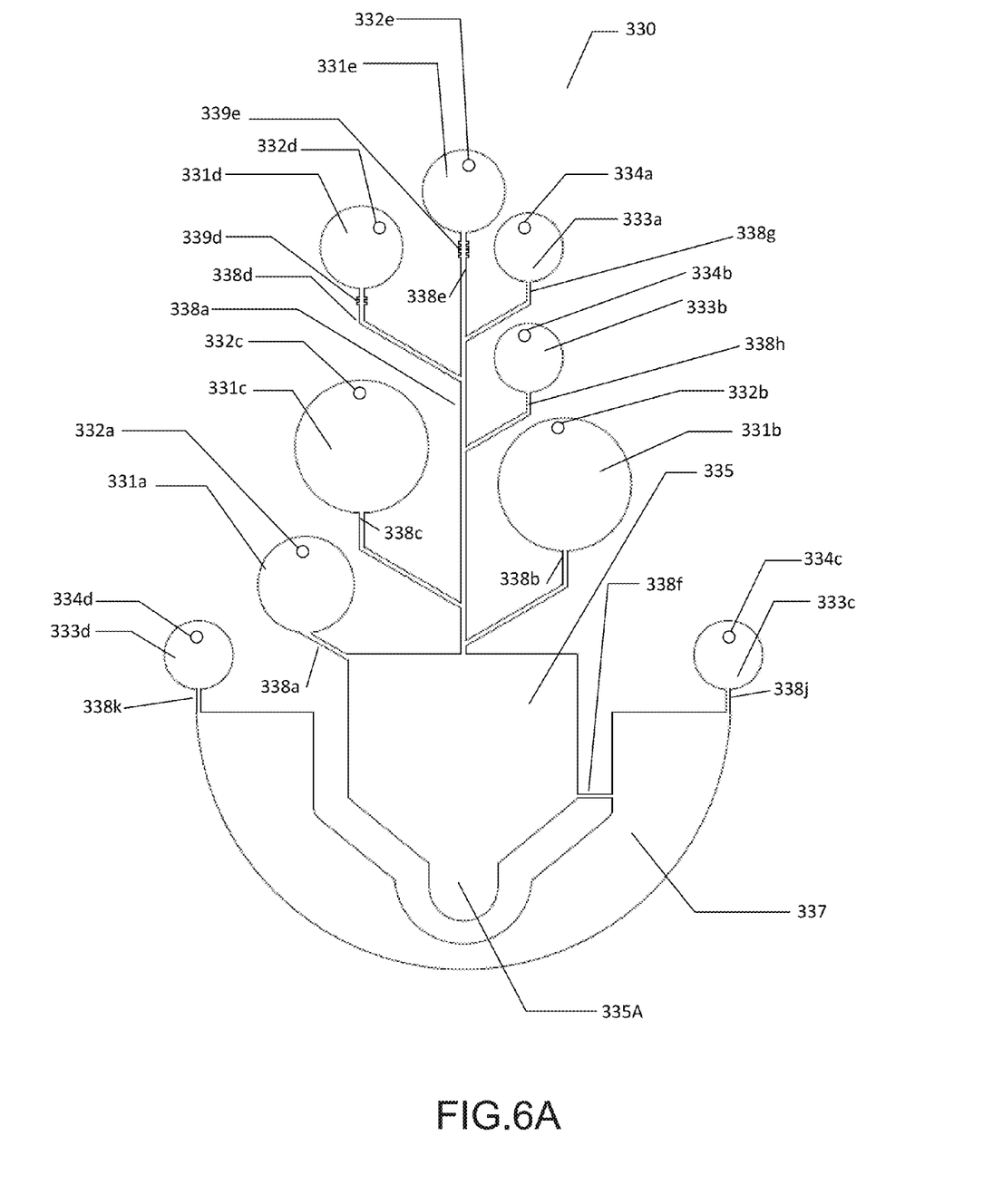
FIG. 6A illustrates the testing mechanism for the second preferred embodiment in accordance with the present invention.

Referring to FIGS. 5 and 6A, according to the second embodiment of the present invention, the abovementioned disc 320 is used for various kinds of microfluidic medicaments/reagents to mix and react so that the reactants can coagulate. The abovementioned disc 320 has at least one fixed structure 326 and at least one testing unit 330. The fixed structure 326 is used to fix the disc 320 on the revolving device 316 so that it can create centrifugal effect, and the disc 320 is replaceable. Moreover, the disc 320 is disposable so that it can avoid being polluted by the specimens and reagents, and this can greatly enhance the reliability of the test and can prevent direct contact with the dosing module 310 and the testing module 340 so as to prolong the life of the overall equipment. Furthermore, the appearance design of the testing unit 330 further includes one dendriform appearance, which means more the testing units 330 can be accommodated in the disc 320, and each testing unit 330 can be views as one testing procedure, so that multiple testing procedures can be executed synchronically.

The abovementioned testing unit 330 is constructed by at least one transparent substrate which is built through laser, carving or injection molding. The testing unit 330 includes multiple feeding chambers 331*a*, 331*b*, 331*c*, 331*d*, 331*e*, multiple feeding apertures 332*a*, 332*b*, 332*c*, 332*d*, 332*e*, multiple vent chambers 333*a*, 333*b*, 333*c*, 333*d*, multiple vent apertures 334a, 334b, 334c, 334d, at least one reaction chamber 335, at least one waste chamber 337, multiple microfluidic channels 338a, 338b, 338c, 338d, 338e, 338f, 338g, 338h, 338j, 338k, and multiple capillary valves 339d, 339e. The abovementioned vent chamber 333a, 333b, 333c, 333d enables the fluid to flow in centrifugal state by connecting to the atmosphere through the vent apertures 334a, 334b, 334c, 334d. The abovementioned dosing component 314 can inject the microfluids to corresponding feeding chambers 331a, 331b, 331c, 331d, 331e for accommodating by way of the feeding apertures 332a, 332b, 332c, 332d, 332e. Wherein, the microfluids that the dosing component 314 can inject are RBC, antibody/plasma, LIM, polybrene/PEI, resuspending solution, etc. In addition, the abovementioned reaction chamber 335 respectively receives the microfluidic reagents from the feeding chambers 331a, 331b, 331c, 331d, 331e, and the accommodating space of the reaction chamber 335 includes at least one reaction testing zone 335A to provide a reaction space for the specimens and reagents, and is used to save most of the reactant of the specimens and other reagents so as to allow the image sensing component 345 to collect the images of the reactants' coagulations in the reaction testing zone 335A.

Moreover, the abovementioned waste chamber 337 is adjacent to the reaction chamber 335 so as to receive the overflowing microfluids from the reaction chamber 335 under centrifugal state. The abovementioned microfluidic channels 338a, 338b, 338c, 338d, 338e are used to respectively connect the feeding chambers 331a, 331b, 331c, 331d, 331e and the reaction chamber 335. The microfluidic channels 338g, 338h are used to respectively connect with the vent chambers 333a, 333b and the reaction chamber 335. The microfluidic channels 338j, 338k are used to respectively connect with the vent chambers 333c, 333d and the waste chamber 337. The microfluidic channel 338f is used to connect with the reaction chamber 335 and the waste chamber 337. Wherein, the microfluidic channels 338a, 338b, 338c, 338d, 338g, 338h are connected to the microfluidic channel 338e respectively so that they can enter the reaction chamber 335 through the microfluidic channel 338e. Moreover, the abovementioned microfluidic channels 338a, 338b, 338c, 338d, 338f, 338g, 338h respectively has a specific joint angle, which can be designed according to the reagents' characteristic, and by controlling the centrifugal rotational speed and the discharging speed of the reagents, it can prevent reverse of the overflowing fluids. Wherein, the joint angle of the microfluidic channel 338a and the feeding chamber 331a is a tangential angle, and by way of tangent line to circle, it lowers the surface resistance of the microfluids and to flow out of the feeding chamber 331a. The microfluidic channels 338b, 338c, 338d, 338g, 338h have a bending angle which is used to control the flowing speed of the microfluids when it flows into the microfluidic channel 338e. The microfluidic channel 338f which connects the reaction chamber 335 and the waste chamber 337 forms a level inclination at the jointing area. The exit of the microfluidic channel 338f near the waste chamber 337 should be higher than the entrance of the microfluidic channel 338f near the reaction chamber 335 to prevent reverse flow.

Figure 6B:
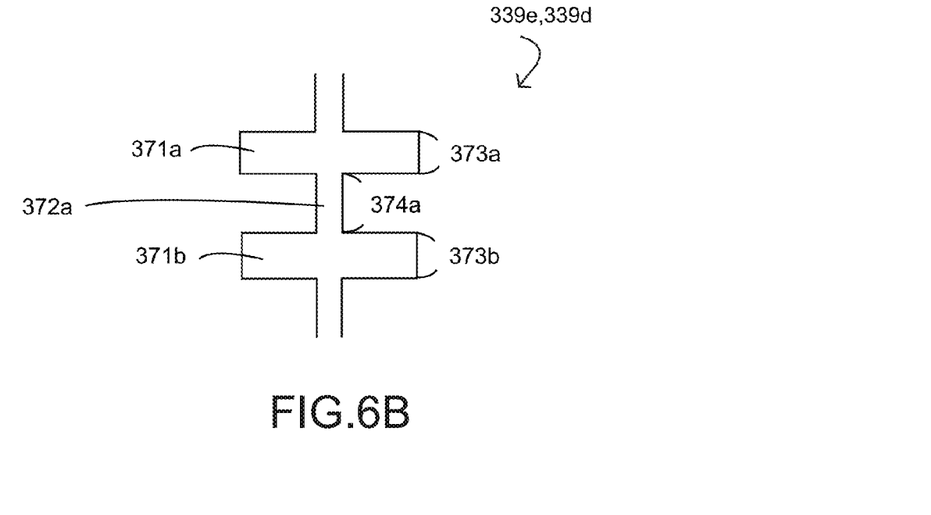
FIG. 6B illustrates the capillary valve of the testing mechanism for the second preferred embodiment in accordance with the present invention.

Referring to FIGS. 6A and 6B, the abovementioned microfluidic channels 338d, 338e on the entrances of the feeding chambers 331d, 331e respectively have the capillary valves 339d, 339e to slow down the speed of the microfluids coming out of the feeding chambers 331d, 331e in order to control the discharge of the medicaments. In addition, the abovementioned capillary valve 339d includes multiple convex channels 371a, 371b and at least one cavernous channel 372a, and they are connected in interlocked arrangement, forming a serrated appearance. Wherein, the diameter of the cavernous channel 372a is smaller than or equal to the microfluidic channel 338d, and is better when it is 100 micrometer. The diameters of the convex channels 371a, 371b are bigger than that of the microfluidic channel 338d, and they are better when their diameters are 300 micrometer. The proportion ranges of the diameters of the convex channels 371a, 371b to that of the cavernous channel 372a are around 2:1-5:1, while 3:1 is better. Moreover, the better ratios of the diameter lengths 373a, 373b of the convex channels 371a, 371b to the diameter length 374a of the cavernous 372a are 1:1, and the lengths are 100 micrometer.

Referring to FIG. 6A, according to the second embodiment of the present invention, the present invention provides an example. The microfluidic medicament/reagent is injected into an assigned chamber, and a first centrifugal procedure (600-800 rpm, 1-10 sec) is carried out on the disc 320 by the revolving component 316. RBC is guided from the feeding chamber 331a into the reaction chamber 335, and antibody/plasma, LIM are respectively guided into the reaction chamber 335 from the feeding chamber 331b, 331c. Then the revolving component 316 reciprocates the disc 320 to proceed a first mixing procedure (reciprocating angle 10-360 degrees, reciprocating time 1-10 times) to mix RBC, antibody/plasma, and LIM. Then, a second centrifugal procedure (600-1000 rpm, 1-10 sec) is proceeded. polybrene/PEI is led out of the feeding chamber 331d to the reaction chamber 335, and the revolving component 316 reciprocates the disc 320 to carry out a second mixing procedure (reciprocating angle 10-360 degrees, reciprocating time 1-10 times) so as to increase the coagulation. Then, a third centrifugal procedure (600-1500 rpm, 1-10 sec) is proceeded to separate the unreacted supernatant. Most of the RBC and agglutinated complex are left in the reaction testing zone 335A, and at the same time the extra reaction fluid will overflow to the waste chamber 337 from the microfluidic channel 338f. Then a fourth centrifugal procedure (600-2000 rpm, 1-10 sec) is proceeded. Resuspending solution is led out of the feeding chamber 331e to the reaction chamber 335, and finally a third mixing procedure (reciprocating angle 10-360 degrees, reciprocating time 1-10 times) is carried out to neutralize the reaction of polybrene/PEI and to break down the false reacted RBC-antibody complex.

Figure 7A:
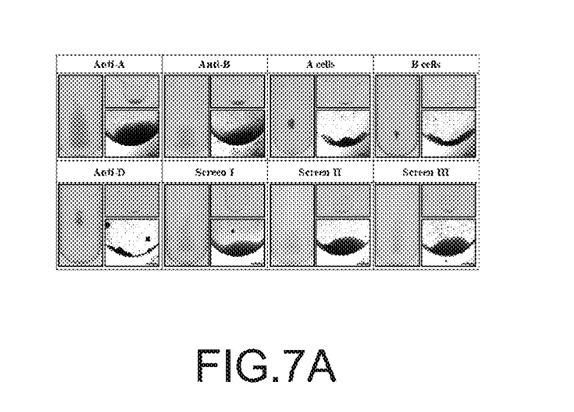
FIG. 7A shows the results of RBC and plasma from the subject with blood type O reacting with anti-A antibody, anti-B antibody, A cells, B cells, anti-D antibody, screening cell I, screening cell II, and screening III through the disc testing in the second preferred embodiment in accordance with the present invention.
Figure 7B:
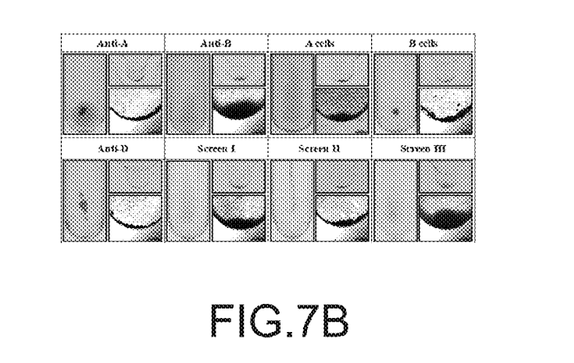
FIG. 7B shows the results of RBC and plasma from the subject with blood type A reacting with anti-A antibody, anti-B antibody, A cells, B cells, anti-D antibody, screening cell I, screening cell II, and screening III through the disc testing in the second preferred embodiment in accordance with the present invention.

Referring to FIGS. 4A and 4B, according to the second embodiment, the abovementioned image sensing component 345 includes one image collecting component. The image sensing component 345 is used to collect the images of the reactant's coagulation, shown in FIGS. 7A and 7B, in the reaction testing zone 335A, and transforms it into an image signal. FIG. 7A shows the blood typing results of a subject with blood type O, and the result is identical to the clinical test tube examination. When RBC is classified, it doesn't agglutinate with anti-A and anti-B antiserum. On the other hand, the serum agglutinates with A cells and B cells. The blood type of the subject is Rh positive, therefore, its RBC agglutinate with anti-D antiserum. Irregular antibody screening shows that the serum from the subject with blood type O does not react with Screen I, II, and III cells. Moreover, FIG. 7B is a diagram showing the examination result of subjects with A blood type's RBC and serum. The result is identical to the clinical test tube examination. In the part of classifying RBC, it agglutinates with anti-A antiserum. In the part of classifying serum, it agglutinates with B cells. In the part of classifying Rh, it agglutinates with anti-D antiserum. Irregular antibody screening shows that the serum from the subject does not react with Screen I and III cells, and it contains $Mi^a$ antibody so it will react with Screen II cells weakly. The reagent's coagulation in the reaction testing zone 335A changes with the reagents, so that the images received by image sensing component 345 also changes with the reactant's coagulations. Moreover, the abovementioned analysis component 352 further includes a default database to provide corresponding images of specific reagents' coagulation so as to receive the image signal from the image sensing component 345 in order to calculate, analyze, compare and contrast the data from the default database, and then the relevant information is shown by the display component 356 of the control component 354.

Although specific embodiments have been illustrated and described, it will be obvious to those skilled in the art that various modifications may be made without departing from what is intended to be limited solely by the appended claims.

What is claimed is:

1. A multichannel microfluidic disc which has at least one testing mechanism, the testing mechanism comprising:
   at least one feeding chamber, being an accommodating space storing microfluids imported from an exterior;
   at least one reaction chamber, being a reacting space receiving the microfluids discharged from the feeding chamber under centrifugal state to allow the microfluids to carry out reaction;
   at least one waste chamber, receiving the microfluids from the reaction chamber under centrifugal state; and
   a plurality of microfluidic channels, connecting the feeding chamber with the reaction chamber and connecting the reaction chamber and the waste chamber respectively, wherein a specific joint angle at the connection between the microfluidic channel and the feeding chamber controls discharging rate of the microfluids through a centrifugal rotational speed and prevents reverse flow of the microfluids, wherein a capillary valve at the connection between the microfluidic channel and the feeding chamber controls the discharging rate of the microfluids through the centrifugal rotational speed and prevents reverse flow of the microfluids, wherein the capillary valve forms an interlocked connection of at least one convex channel and at least one cavernous channel on the microfluidic channel to form a serrated appearance, wherein the diameter of the convex channel is bigger than that of the cavernous channel, and the diameter of the convex channel is also bigger than that of the microfluidic channel, wherein the ratio for the diameter of the convex channel and that of the cavernous channel is 2:1-5:1.

2. The multichannel microfluidic disc according to claim 1, wherein the testing mechanism further comprises at least one vent chamber being a space connecting the atmosphere to allow the microfluids to flow in the testing mechanism under centrifugal state.

3. The multichannel microfluidic disc according to claim 1, wherein the reaction chamber comprises at least one reaction testing zone being used to store the reactant of the microfluids and collect and analyze the images of reactant coagulations.

4. The multichannel microfluidic disc according to claim 1, wherein the microfluidic channel has a specific bending angle to control the discharging rate of the microfluids through the centrifugal rotational speed and prevents reverse flow of the microfluids.

5. A multichannel microfluidic disc testing system, comprising:
   a disc module, used to receive a plurality of microfluidic reagents, by way of centrifugal effect, the microfluidic reagents being mixed in the disc module to produce chemical effect and form reactants, wherein the disc module comprises at least one testing unit, the testing unit further comprises:
   a plurality of feeding chambers, used to respectively receive and store a plurality of microfluidic reagents provided by the dosing module;
   at least one reaction chamber, used to respectively receive the microfluidic reagents discharged by the feeding chambers to carry out the reactions and form the reactants, wherein an accommodating space of the reaction chamber further comprises at least one reaction testing zone to provide a reaction space for the microfluidic reagents and store the reactants to allow the imaging module to collect the images of the reactant coagulations in the reaction testing zone;
   a waste chamber, receiving the microfluids from the reaction chamber in centrifugal state; and
   a plurality of microfluidic channels, used respectively to connect the feeding chambers and the reaction chamber; wherein the testing unit is a dendriform appearance, and the microfluidic channels are the branches of the dendriform appearance, and the feeding chambers are located at the end of the branches, and the reaction chamber is located at the root of the dendriform appearance, wherein the microfluidic channels has a first microfluidic channel and a plurality of second microfluidic channels, the first microfluidic channel is used as a main trunk of the dedriform appearance and is connected with the reaction chamber, the second microfluidic channels are treated as the branches of the dedriform appearance and are connected to the first microfluidic channel and the feeding chambers, wherein the second microfluidic channel has a bending angle to control discharging rate of the microfluidic reagents through a centrifugal rotational speed and prevent reverse flow of the microfluidic reagents, wherein a joint angle of the second microfluidic channel and the feeding chamber is a tangential angle, the tangential angle lowers the surface resistance by way of tangent line to circle and leads the microfluids out of the feeding chamber centrifugally;
   a dosing module, located in a specific place on the rotating direction of the disc module, the dosing module providing the microfluidic reagents and centrifugal effect to the disc module; and
   an imaging module, located in a assigned place on the disc module to collect the images of reactant coagulations on the disc module.

6. The multichannel microfluidic disc testing system according to claim 5, wherein the dosing module further comprises:
   at least one dosing device, used to control the placing, loading, transporting and infusing of the microfluids to the disc module; and
   at least one spinning device, used to provide the disc module with the spinning kinetic energy to carry out the centrifugal motion to make the microfluidic reagents mix and react on the disc module by way of centrifugation.

7. The multichannel microfluidic disc testing system according to claim 5, wherein the testing unit comprises a plurality of vent chambers connecting to the atmosphere to allow the microfluidic reagents to flow in centrifugal state.

8. The multichannel microfluidic disc testing system according to claim 5, wherein a capillary valve at the connection between the microfluidic channel and the feeding chamber controls discharging rate of the microfluids through the centrifugal speed and prevents reverse flow of the microfluids, wherein the capillary valve forms at least one convex channel and at least one cavernous channel on the microfluidic channel to form a serrated appearance through their interlocked arrangement.

9. The multichannel microfluidic disc testing system according to claim 8, wherein the diameter of the convex channel is bigger than that of the cavernous channel, and the diameter of the convex channel is also bigger than that of the microfluidic channel, wherein the diameter of the carvernous channel is smaller than or equal to that of the microfluidic channel.

10. The multichannel microfluidic disc testing system according to claim 5, wherein the microfluidic reagents further comprises RBC, antibody/plasma, LIM, polybrene/polyethyleneimine, resuspending solution.

* * * * *